(12) United States Patent
Ochi et al.

(10) Patent No.: US 9,784,672 B2
(45) Date of Patent: Oct. 10, 2017

(54) FOODSTUFF ANALYSIS DEVICE

(71) Applicant: Panasonic Intellectual Property Management Co., Ltd., Osaka (JP)

(72) Inventors: Kazuhiro Ochi, Kyoto (JP); Tatsuya Takahashi, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 98 days.

(21) Appl. No.: 14/418,056

(22) PCT Filed: Nov. 6, 2013

(86) PCT No.: PCT/JP2013/006540
§ 371 (c)(1),
(2) Date: Jan. 28, 2015

(87) PCT Pub. No.: WO2014/103130
PCT Pub. Date: Jul. 3, 2014

(65) Prior Publication Data
US 2015/0260644 A1    Sep. 17, 2015

(30) Foreign Application Priority Data
Dec. 27, 2012    (JP) ................. 2012-286268

(51) Int. Cl.
*G01J 5/00*    (2006.01)
*G01N 21/31*    (2006.01)
(Continued)

(52) U.S. Cl.
CPC ........... *G01N 21/314* (2013.01); *G01N 21/27* (2013.01); *G01N 21/359* (2013.01);
(Continued)

(58) Field of Classification Search
CPC .. G01N 33/02; G01N 21/3563; G01N 21/255; G01N 21/27; G01N 21/31;
(Continued)

(56) References Cited

U.S. PATENT DOCUMENTS

| 4,692,621 A | 9/1987 | Passaro et al. |
| 5,258,620 A | 11/1993 | Sueyasu et al. |

(Continued)

FOREIGN PATENT DOCUMENTS

| CN | 202421065 U | 9/2012 |
| JP | 63-501593 A | 6/1988 |

(Continued)

OTHER PUBLICATIONS

Huang et al., "Near infrared spectroscopy for on/in-line monitoring of quality in foods and beverages: A review," 2008, Journal of Food Engineering, vol. 87, pp. 303-313.*

(Continued)

*Primary Examiner* — Kiho Kim
(74) *Attorney, Agent, or Firm* — McDermott Will & Emery LLP

(57) ABSTRACT

Provided is a foodstuff analysis device capable of readily calculating calories or component weights. The foodstuff analysis device has a light-emitting unit, a light-receiving section, and a control unit. The light-emitting unit irradiates light including at least some wavelengths among wavelengths in the range 700-1,100 nm, on to an analysis target. The light-receiving section receives light reflected from the analysis target. The control unit calculates the absorbance of light received by the light-receiving section, and calculates the calories of the analysis target on the basis of the calculated absorbance and on the basis of the correlation between absorbance and calories.

6 Claims, 5 Drawing Sheets

(51) Int. Cl.
*G01N 33/02* (2006.01)
*G01N 21/359* (2014.01)
*G01N 21/27* (2006.01)
*G01N 21/3563* (2014.01)

(52) U.S. Cl.
CPC ......... *G01N 21/3563* (2013.01); *G01N 33/02* (2013.01); *G01N 2201/12* (2013.01)

(58) Field of Classification Search
CPC ............. G01N 21/314; G01N 21/3554; G01N 2201/061; G01N 2201/06113; G01N 2201/12; G01N 5/00
USPC ...................................................... 250/338.1
See application file for complete search history.

(56) References Cited

U.S. PATENT DOCUMENTS

| | | | |
|---|---|---|---|
| 2002/0084415 A1 | 7/2002 | Kawano et al. | |
| 2002/0168046 A1* | 11/2002 | Hansen | G01N 23/06 378/51 |
| 2007/0218174 A1 | 9/2007 | Hanamatsu et al. | |
| 2008/0291456 A1* | 11/2008 | Ghislain | G01N 29/022 356/450 |
| 2009/0152475 A1* | 6/2009 | Sasaki | G01J 3/10 250/492.1 |
| 2009/0184247 A1* | 7/2009 | Shimazu | G01N 21/3563 250/339.11 |
| 2011/0001967 A1* | 1/2011 | Utsunomiya | G01N 21/553 356/319 |
| 2012/0199742 A1* | 8/2012 | Wagner | C12N 5/0612 250/338.1 |
| 2012/0228519 A1* | 9/2012 | Gilmore | G01N 21/645 250/459.1 |
| 2013/0010294 A1* | 1/2013 | Matsuda | G01N 21/3563 356/326 |

FOREIGN PATENT DOCUMENTS

| | | |
|---|---|---|
| JP | 04-047254 A | 2/1992 |
| JP | 08-075642 A | 3/1996 |
| JP | 08-233735 A | 9/1996 |
| JP | 10-160666 A | 6/1998 |
| JP | 10-339698 A | 12/1998 |
| JP | 2002-122538 A | 4/2002 |
| JP | 2005-292128 A | 10/2005 |
| JP | 2006-238849 A | 9/2006 |
| JP | 2007-215430 A | 8/2007 |
| JP | 2008-151548 A | 7/2008 |

OTHER PUBLICATIONS

Hans Buning-Pfaue, "Analysis of water in food by near infrared spectroscopy," 2003, Food Chemistry, vol. 82, pp. 107-115.*

Bajwa, S.G. et al., "Spectroscopic evaluation of the nutrient value of ground beef patties", Journal of Food Engineering, 92, Dec. 31, 2008, 454-460.

Chinese Office Action issued in Chinese Application No. 201380043617.5, dated May 3, 2016.

Kandaswamy, J. et al., "Chemometric Modeling of Fat, Cholesterol and Caloric Content of Fresh and Cooked Ground Beef with NIR Reflectance Spectroscopy", Sensors for Industry Conference, Feb. 8, 2005-Feb. 10, 2005, pp. 52-58.

Lanza, E., "Determination of Moisture, Protein, Fat, and Calories in Raw Pork and Beef by Near Infrared Spectroscopy", Journal of Food Science, vol. 48, No. 2, 1983, pp. 471-474.

Extended European Search Report issued in European Application No. 13866722.5, dated Sep. 29, 2015.

English Translation of International Preliminary Report on Patentability issued in International Application No. PCT/JP2013/006540 dated Jun. 30, 2015.

International Search Report issued in PCT/JP2013/006540, dated Dec. 10, 2013, with English translation.

* cited by examiner

FOODSTUFF ANALYSIS DEVICE

RELATED APPLICATIONS

This application is the U.S. National Phase under 35 U.S.C. §371 of International Application No. PCT/JP2013/006540, filed on Nov 6, 2013, which in turn claims the benefit of Japanese Application No. 2012-286268, filed on Dec. 27, 2012, the disclosures of which Applications are incorporated by reference herein.

TECHNICAL FIELD

The present invention relates to a foodstuff analysis device.

BACKGROUND ART

Patent document 1 discloses one example of a conventional process for calculating the calories of a foodstuff and the weights of components of the foodstuff. In the conventional process for calculating the calories and the weights of components, a foodstuff is crushed. The process chemically analyzes each component in the crushed foodstuff and calculates the weight of each component in the foodstuff. The calories are calculated using the weights of the components.

PRIOR ART DOCUMENT

Patent Document

Patent Document 1: Japanese Laid-Open Patent Publication No. 2007-215430

SUMMARY OF THE INVENTION

Problems that are to be Solved by the Invention

The above process for calculating calories and weights of components performs a chemical analysis. Therefore, the calculation of calories or weights of components takes time and effort.

The present invention is based on the above background. It is an object of the present invention to provide a foodstuff analysis device capable of readily calculating calories or weights of components.

Means for Solving the Problem

One aspect of the present invention is a foodstuff analysis device. The foodstuff analysis device includes a light emitter that irradiates an analysis subject with light having a wavelength included in a range from 700 nm to 1100 nm, a light receiver that receives at least one of light reflected from the analysis subject and light passing through the analysis subject, a calculator that calculates an absorption amount of light received by the light receiver, and an analyzer that performs at least one of a calculation of calories of the analysis subject based on a correlation of the absorption amount of light and calorie and the absorption amount of light calculated by the calculator, and a calculation of a component amount of the analysis subject based on a correlation of the absorption amount of light and the component amount of a foodstuff and the absorption amount of light calculated by the calculator.

The analyzer calculates the calories of the analysis subject using the absorption amount of some of the light reflected from the analysis subject and including a wavelength from 700 nm to 1100 nm and/or the absorption amount of the light passing through the analysis subject and including a wavelength from 700 nm to 1100 nm. This simplifies the calculation of calories compared to when a chemical means is used to calculate calories.

Preferably, the calculator calculates the absorption amount of light having a specified wavelength in the light received by the light receiver, and the specified wavelength is at least one of wavelength ranges from 940 to 1020 nm, 910 to 940 nm, 890 to 930 nm, 970 to 1000 nm, 1000 to 1030 nm, 1030 to 1060 nm, 740 to 770 nm, 1010 to 1060 nm, and 890 to 950 nm.

Preferably, the specified wavelength includes at least one of the wavelength ranges from 940 to 1020 nm and from 910 to 940 nm.

Preferably, the foodstuff analysis device further includes a wavelength limiter that limits a wavelength range of the light emitted from the light emitter to a specified range in which the specified wavelength is the main component.

Preferably, the wavelength limiter limits the wavelength range of the light to the specified range before the light emitted from the light emitter reaches the analysis subject.

Preferably, the wavelength limiter limits the wavelength range of the light to the specified range after the light emitted from the light emitter reaches the analysis subject and before the light emitted from the light emitter is received by the light receiver.

Preferably, the light emitter irradiates the analysis subject only with light in the specified range in which the specified wavelength is the main component.

Preferably, the foodstuff analysis device further includes a detector that performs at least one of a measurement of weight of the analysis subject and a measurement of volume of the analysis subject. The analyzer calculates the calories of the analysis subject or the amount of the component of the analysis subject using a measurement result of the detector.

Effects of the Invention

The present foodstuff analysis device readily calculates calories or weights of components.

EMBODIMENTS OF THE INVENTION

The structure of a foodstuff analysis device 1 will now be described with reference to FIGS. 1 and 2. The foodstuff analysis device 1 calculates the calories of an analysis subject S. The analysis subject S includes food. The food includes solid and liquid substances.

Figure 1:
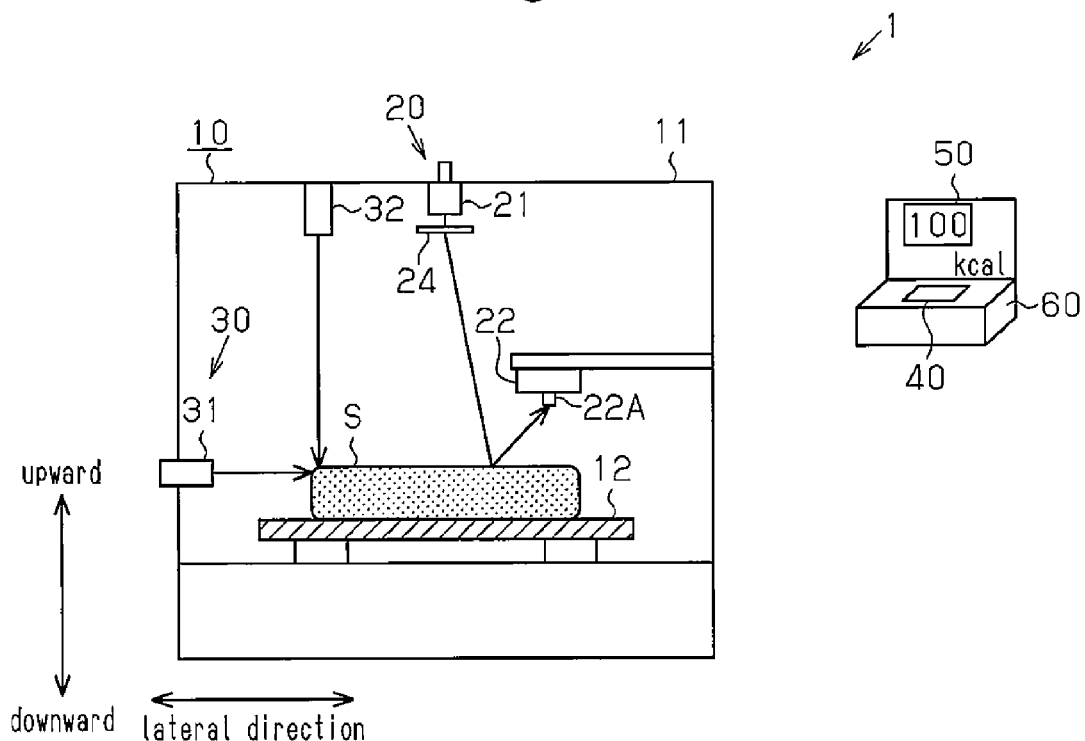
FIG. 1 is a schematic diagram of a first embodiment of a foodstuff analysis device according to the present invention showing the overall structure of the foodstuff analysis device.

As shown in FIG. 1, the foodstuff analysis device 1 includes a main body 10, a measurement unit 20, a position sensor 30, a controller 60, an operation unit 40, and a display 50. The controller 60 corresponds to a "calculator" and an "analyzer".

The main body 10 includes a case 11 and a sample plate 12.

The sample plate 12 and the analysis subject S are located in the case 11. The case 11 includes a door (not shown). When a user closes the door, the interior is shielded from light.

Figure 2:
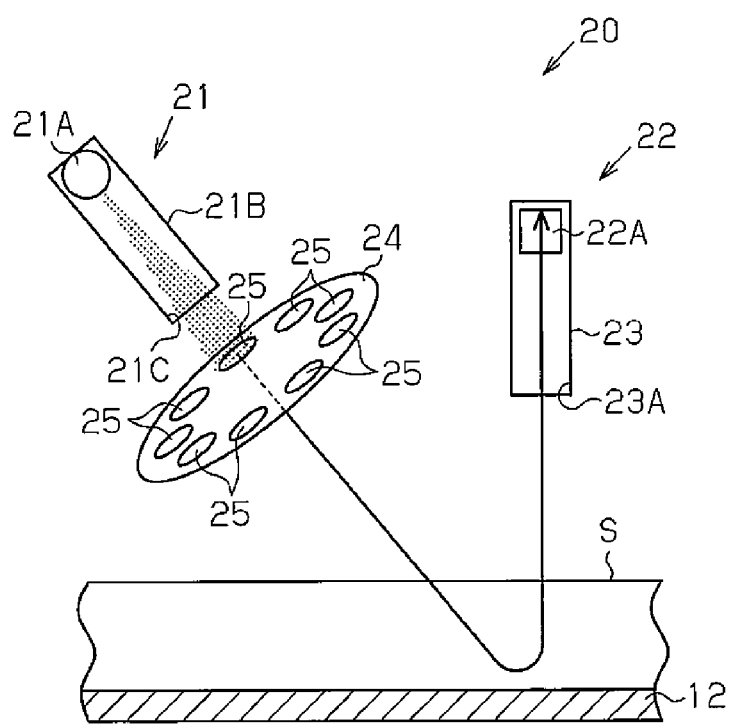
FIG. 2 is a schematic diagram of a measurement unit of the first embodiment according to the present invention showing the overall structure of the measurement unit.

As shown in FIG. 2, the measurement unit 20 includes a light emitter 21, a light receiver 22, and a wavelength limiter 24.

The light emitter 21 includes a light source 21A and a cylinder portion 21B. The light emitter 21 is located above the sample plate 12. The light emitter 21 irradiates the analysis subject S located on an upper surface of the sample plate 12 with light from the light source 21A.

The light source 21A emits light having a wavelength included in a range from 700 to 1100 nm, which is near-infrared light. The light source 21A may include, for example, a halogen lamp.

The cylinder portion 21B is cylindrical. An upper end of the cylinder portion 21B accommodates the light source 21A. A lower end of the cylinder portion 21B is directed toward the analysis subject S. The lower end of the cylinder portion 21B includes an opening 21C. The interior of the cylinder portion 21B includes a specular surface. The cylinder portion 21B blocks the light of the light source 21A. Thus, the cylinder portion 21B guides the light from the light source 21A toward the opening 21C.

The light receiver 22 includes a light reception element 22A and a cylinder portion 23.

The light reception element 22A is located above the sample plate 12. The light emitter 21 irradiates the analysis subject S with light. Then, the light reception element 22A receives diffused and reflected light from the analysis subject S. The light reception element 22A transmits a signal to the controller 60 in correspondence with the received light. The light reception element 22A may include, for example, a silicon element.

The cylinder portion 23 is cylindrical. An upper end of the cylinder portion 23 accommodates the light reception element 22A. A lower end of the cylinder portion 23 is directed toward the analysis subject S. The lower end of the cylinder portion 23 includes an opening 23A. The light, which is reflected and diffused by the analysis subject S, is received by the light reception element 22A through the opening 23A.

The wavelength limiter 24 includes a plurality of filters 25. Each of the filters 25 limits the wavelength of the light from the light source 21A to a specified range that is unique to the filter 25. The wavelength limiter 24 limits the wavelength of the light from the light source 21A to the wavelength range unique to one of the filters 25 that is arranged at the opening 21C. The analysis subject S is entirely irradiated with the light having passed through the filter 25. Thus, the light, which has been reflected and diffused by the analysis subject S and received by the light receiver 22, indicates the entire components of the analysis subject S.

The specified range includes a first specified range, a second specified range, a third specified range, a fourth specified range, a fifth specified range, a sixth specified range, a seventh specified range, an eighth specified range, and a ninth specified range.

The first specified range has a specified wavelength included in a range from 940 to 1020 nm as the main component. The first specified range is a predetermined wavelength range including at least the specified wavelength. Preferably, the specified wavelength of the first specified range is 970 nm.

The second specified range has a specified wavelength included in a range from 910 to 940 nm as the main component. The second specified range is a predetermined wavelength range including at least the specified wavelength. Preferably, the specified wavelength of the second specified range is 930 nm.

The third specified range has a specified wavelength included in a range from 890 to 930 nm as the main component. The third specified range is a predetermined wavelength range including at least the specified wavelength. Preferably, the specified wavelength of the third specified range is 905 nm.

The fourth specified range has a specified wavelength included in a range from 970 to 1000 nm as the main component. The fourth specified range is a predetermined wavelength range including at least the specified wavelength. Preferably, the specified wavelength of the fourth specified range is 980 nm.

The fifth specified range has a specified wavelength included in a range from 1000 to 1030 nm as the main component. The fifth specified range is a predetermined wavelength range including at least the specified wavelength. Preferably, the specified wavelength of the fifth specified range is 1020 nm.

The sixth specified range has a specified wavelength included in a range from 1030 to 1060 nm as the main component. The sixth specified range is a predetermined wavelength range including at least the specified wavelength. Preferably, the specified wavelength of the sixth specified range is 1040 nm.

The seventh specified range has a specified wavelength included in a range from 740 to 770 nm as the main component. The seventh specified range is a predetermined wavelength range including at least the specified wavelength. Preferably, the specified wavelength of the seventh specified range is 760 nm.

The eighth specified range has a specified wavelength included in a range from 1010 to 1060 nm as the main component. The eighth specified range is a predetermined wavelength range including at least the specified wavelength. Preferably, the specified wavelength of the eighth specified range is 1030 nm.

The ninth specified range has a specified wavelength included in a range from 890 to 950 nm as the main component. The ninth specified range is a predetermined wavelength range including at least the specified wavelength. Preferably, the specified wavelength of the ninth specified range is 920 nm.

When the filter 25 that corresponds to the first specified range is arranged at the opening 21C, the analysis subject S is irradiated with the light including the wavelength limited to the first specified range.

When the filter 25 that corresponds to the second specified range is arranged at the opening 21C, the analysis subject S is irradiated with the light including the wavelength limited to the second specified range.

When the filter 25 that corresponds to the third specified range is arranged at the opening 21C, the analysis subject S is irradiated with the light including the wavelength limited to the third specified range.

When the filter 25 that corresponds to the fourth specified range is arranged at the opening 21C, the analysis subject S is irradiated with the light including the wavelength limited to the fourth specified range.

When the filter 25 that corresponds to the fifth specified range is arranged at the opening 21C, the analysis subject S is irradiated with the light including the wavelength limited to the fifth specified range.

When the filter 25 that corresponds to the sixth specified range is arranged at the opening 21C, the analysis subject S is irradiated with the light including the wavelength limited to the sixth specified range.

When the filter 25 that corresponds to the seventh specified range is arranged at the opening 21C, the analysis subject S is irradiated with the light including the wavelength limited to the seventh specified range.

When the filter 25 that corresponds to the eighth specified range is arranged at the opening 21C, the analysis subject S is irradiated with the light including the wavelength limited to the eighth specified range.

When the filter 25 that corresponds to the ninth specified range is arranged at the opening 21C, the analysis subject S is irradiated with the light including the wavelength limited to the ninth specified range.

As shown in FIG. 1, the position sensor 30 includes a first position sensor 31 and a second position sensor 32.

The first position sensor 31 is coupled to an inner surface of the case 11. The first position sensor 31 is arranged in the lateral direction of the sample plate 12. The first position sensor 31 provides the controller 60 with a signal that corresponds to the distance from the analysis subject S.

The second position sensor 32 is coupled to the inner surface of the case 11. The second position sensor 32 is located above the sample plate 12. The second position sensor 32 provides the controller 60 with a signal that corresponds to the distance from the analysis subject S.

The operation unit 40 includes a measurement start button (not shown in the drawing). When the user pushes the measurement start button, the operation unit 40 provides the controller 60 with a signal indicating a start of measurement.

The display 50 includes a liquid crystal window. The display 50 shows a calculation result of the calories of the analysis subject S on the liquid crystal window.

The controller 60 is connected to the measurement unit 20, the position sensor 30, the operation unit 40, and the display 50 by cables (not shown). The controller 60 calculates the calories of the analysis subject S based on the signal from the light reception element 22A. The controller 60 calculates the lateral position of the analysis subject S based on the signal from the first position sensor 31. The controller 60 calculates the longitudinal position of the analysis subject S based on the signal from the second position sensor 32. The controller 60 changes the filters 25 based on a predetermined program.

The procedures for measuring the calories of the analysis subject S performed by the controller 60 will now be described.

When receiving the signal indicating a start of measurement from the operation unit 40 operated by the user, the controller 60 sequentially performs procedures 1 to 10, which are described below, to calculate the calories of the analysis subject S.

Procedure 1: The controller 60 detects the position of the analysis subject S based on the signals from the position sensor 30. More specifically, the controller 60 calculates the distance from the analysis subject S to the light emitter 21 and the distance from the analysis subject S to the light reception element 22A.

Procedure 2: The controller 60 sets the position and the angle of the light emitter 21 based on the position of the analysis subject S. Thus, the analysis subject S is entirely irradiated with the light that has passed through the filter 25.

Procedure 3: The controller 60 sets the filter 25 that corresponds to the first specified range at the opening 21C.

Procedure 4: The controller 60 drives the light emitter 21 of the measurement unit 20 to irradiate the analysis subject S with the near-infrared light.

Procedure 5: The controller 60 detects the signal based on the amount of the light received from the light receiver 22 a number of times.

Procedure 6: The controller 60 sets the filter 25 that corresponds to the second specified range at the opening 21C when a predetermined period has passed.

Procedure 7: The controller 60 detects the signal based on the amount of the light received from the light receiver 22 a number of times.

Procedure 8: The controller 60 repeatedly performs procedure 6 and procedure 7 on each of the filters 25 that correspond to the third specified range to the ninth specified range.

Procedure 9: The controller 60 calculates the calories of the analysis subject S based on the amount of the light received from the light receiver 22.

Procedure 10: The controller 60 shows the calculated calories on the display 50.

The relationship of each component forming a foodstuff and the absorbance will now be described.

The inventors have discovered the following relationship of each component forming a foodstuff and the absorbance when near-infrared light includes the wavelength from 700 nm to 1100 nm. FIGS. 3 to 6 show the relationship of each component forming a foodstuff and the absorbance under normal temperatures.

Figure 3:
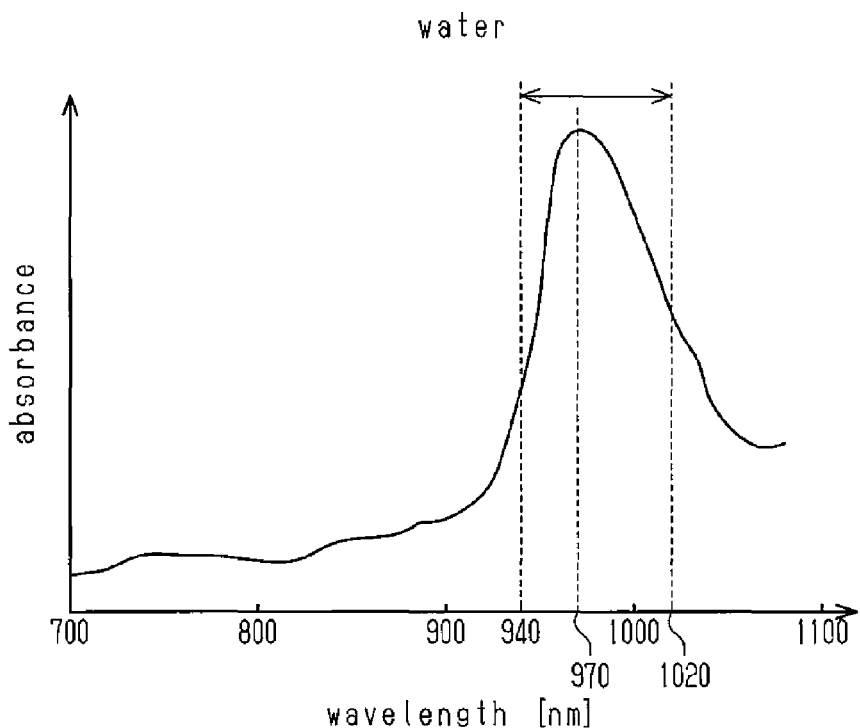
FIG. 3 is a graph showing the relationship of the wavelength and the absorbance of water.

As shown in FIG. 3, water has an absorbance peak at a wavelength of 970 nm. In addition, water, the peak absorbance of which is 970 nm, has the absorbance that is greater at the wavelength from 940 to 1020 nm than at other wavelengths.

Figure 4:
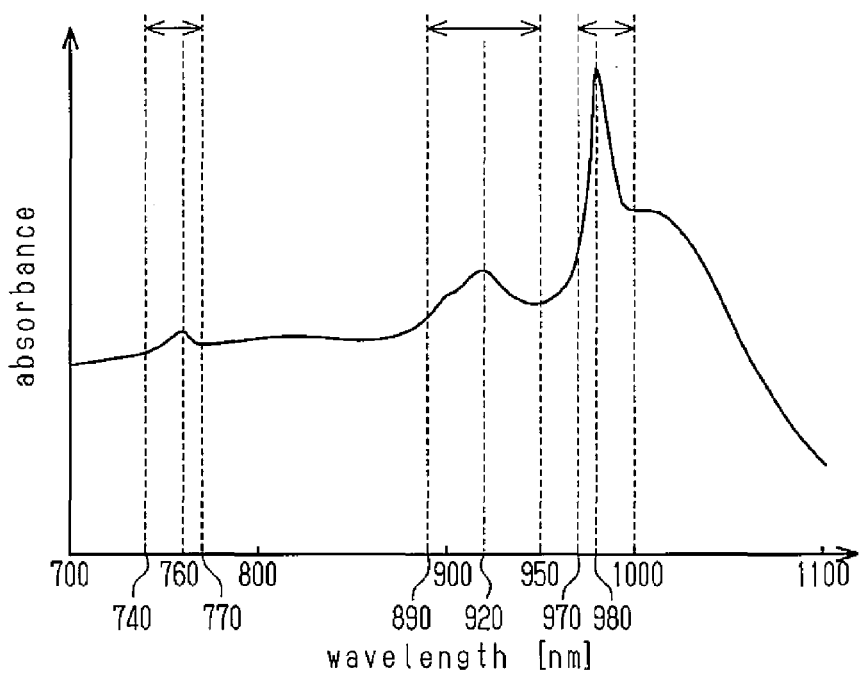
FIG. 4 is a graph showing the relationship of the wavelength and the absorbance of carbohydrate.

As shown in FIG. 4, carbohydrate has absorbance peaks at wavelengths of 760 nm, 920 nm, and 980 nm. In addition, carbohydrate, the peak absorbance of which is 760 nm, has the absorbance that is greater at the wavelength from 740 nm to 770 nm than at other wavelengths. Carbohydrate, the peak absorbance of which is 920 nm, has the absorbance that is greater at the wavelength from 890 nm to 950 nm than at other wavelengths. Carbohydrate, the peak absorbance of which is 980 nm, has the absorbance that is greater at the wavelength from 970 nm to 1000 nm than at other wavelengths.

Figure 5:
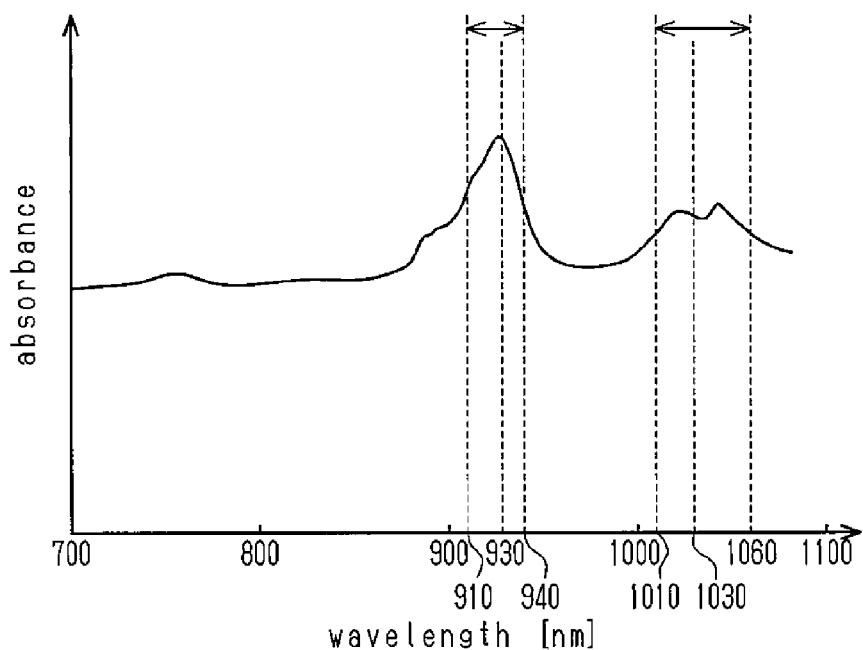
FIG. 5 is a graph showing the relationship of the wavelength and the absorbance of fat.

As shown in FIG. 5, fat has absorbance peaks at wavelengths of 930 nm and 1030 nm. In addition, fat, the peak absorbance of which is 930 nm, has the absorbance that is greater at the wavelength from 910 to 940 nm than at other wavelengths. Fat, the peak absorbance of which is 1030 nm, has the absorbance that is greater at the wavelength from 1010 to 1060 nm than at other wavelengths.

Figure 6:
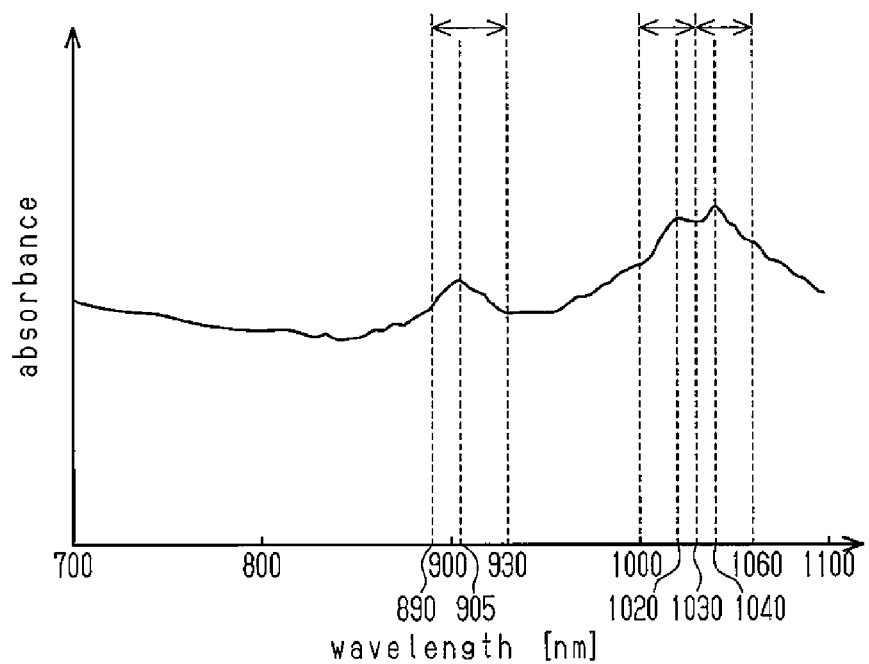
FIG. 6 is a graph showing the relationship of the wavelength and the absorbance of protein.

As shown in FIG. 6, protein has absorbance peaks at wavelengths of 905 nm, 1020 nm, and 1030 nm. In addition, protein, the peak absorbance of which is 905 nm, has the absorbance that is greater at the wavelength from 890 to 930 nm than at other wavelengths. Protein, the peak absorbance of which is 1020 nm, has the absorbance that is greater at the wavelength from 1000 to 1030 nm than at other wavelengths. Protein, the peak absorbance of which is 1040 nm, has the absorbance that is greater at the wavelength from 1030 to 1060 nm than at other wavelengths.

From the above findings, the inventors have created a process for calculating the calories of the analysis subject S. The process uses the absorbance of the wavelength that indicates a larger absorbance than other wavelengths. That is, the inventers compared the calories of a foodstuff calculated by a chemical process with the absorbance of the foodstuff at a specified wavelength included in a range from 700 nm to 1100 nm. The inventors discovered that the calories of the foodstuff calculated by the chemical process correlates with the absorbance of the foodstuff at the specified wavelength included in the range 700 nm to 1100 nm. The invertors obtained a relational equation between the calories of a plurality of foodstuffs calculated by the chemical process and the absorbance of the foodstuffs at the specified wavelength included in the range from 700 nm to 1100 nm. The relational equation is determined using a statistical process, such as the PLS method, the multiple regression analysis, or the factor analysis. The relational equation corresponds to the "correlation".

The controller 60 calculates calories using the above relational equation stored in advance.

The procedures for calculating calories will now be specifically described.

The controller 60 calculates the absorption amount of light and the absorbance corresponding to each specified range based on the amount of received light. The controller 60 calculates the absorbance of each detection result to obtain an average. The controller 60 calculates an average of the absorbance corresponding to each specified range. The controller 60 calculates the calories of the analysis subject S using the average of the absorbance and the relational equation. More specifically, the controller 60 assigns the average of the absorbance into the relational equation to calculate the calories of the analysis subject S.

The operation of the foodstuff analysis device 1 will now be described.

In the conventional process for calculating calories, the analysis subject S is crushed. The process uses a chemical means to calculate the weights of water, carbohydrate, fat, and protein contained in the analysis subject S. The process calculates the calories based on the weights of water, carbohydrate, fat, and protein.

A chemical substance and a device, such as a centrifuge, are used in the conventional process for calculating calories using the chemical means. This complicates the calculation of calories. Additionally, the analysis subject S needs to be crushed.

The foodstuff analysis device 1 uses near-infrared light to calculate the calories of the analysis subject S. This allows calculation of the calories of the analysis subject S without using a chemical substance and a device, such as a centrifuge. Additionally, the calories of the analysis subject S can be calculated without crushing the analysis subject S.

Water absorbs light of wavelengths of 1100 nm or greater in a relatively easy manner. Thus, hardly any light of wavelengths of 1100 nm or greater enters the analysis subject S.

The foodstuff analysis device 1 uses light having a specified wavelength included in the range from 700 to 1100 nm to calculate calories. Thus, such light easily enters the analysis subject S compared to when light having a wavelength of 1100 nm or greater is used to calculate calories. This allows calculation of the calories of the analysis subject S that indicate even the inside of the analysis subject S.

A silicon element, which is used as the light reception element 22A, has a low photosensitivity to the light of wavelengths of 1100 nm or greater. The foodstuff analysis device 1 calculates calories using the light of the specified wavelength included in the range from 700 to 1100 nm. Thus, the foodstuff analysis device 1 may use a silicon element as the light reception element 22A. The price of a silicon element is relatively low. This reduces the cost of the foodstuff analysis device 1.

The foodstuff analysis device 1 includes the wavelength limiter 24. The wavelength limiter 24 limits the range of the wavelength of the light emitted from the light emitter 21 to the specified range in which the specified wavelength is the main component. Therefore, light having a wavelength that is not used for calorie calculation does not reach the light reception element 22A. This simplifies the structure of the foodstuff analysis device 1 as compared to a structure in which the light receiver 22 spectrally measures light of unrestricted wavelengths.

Each of the specified ranges uses the wavelength having a peak, as the main component, that corresponds to one of water, fat, protein, and carbohydrate. Water, fat, protein, and carbohydrate greatly affect calories. This reduces the number of variables used to calculate calories compared to a structure that uses a wide range of wavelengths to calculate calories.

The foodstuff analysis device 1 has the advantages described below.

(1) The controller 60 calculates the calories of the analysis subject S using the absorption amount of light having a wavelength included in the range from 700 nm to 1100 nm, which is reflected from the analysis subject S. This simplifies the calculation of calories compared to when a chemical means is used to calculate calories.

(2) The foodstuff analysis device 1 uses near-infrared light to calculate the calories of the analysis subject S. This allows the foodstuff analysis device 1 to calculate the calories without crushing the analysis subject S.

(3) The controller 60 calculates calories using the absorbance of the wavelengths in the first specified range to the ninth specified range.

The absorbance of the wavelength from 940 nm to 1020 nm clearly indicates water under normal temperatures. The absorbance of the wavelength from 910 nm to 940 nm clearly indicates fat under normal temperatures. The absorbance of the wavelength from 890 nm to 930 nm clearly indicates protein under normal temperatures. The absorbance of the wavelength from 970 nm to 1000 nm clearly indicates carbohydrate under normal temperatures. The absorbance of the wavelength from 1000 nm to 1030 nm clearly indicates protein under normal temperatures. The absorbance of the wavelength from 1030 nm to 1060 nm clearly indicates protein under normal temperatures. The absorbance of the wavelength from 740 to 770 nm clearly indicates carbohydrate under normal temperatures. The absorbance of the wavelength from 1010 to 1060 nm clearly indicates fat under normal temperatures. The absorbance of the wavelength from 890 nm to 950 nm clearly indicates carbohydrate under normal temperatures. The center of the peak of the wavelength that clearly indicates each component shifts by 10 nm to 20 nm depending on a condition, such as temperature. Therefore, the light having the wavelength that clearly indicates each component may be used in accordance with the condition in which measurement is actually performed. This further improves the accuracy of calorie calculation.

The absorbance of the wavelengths in the above ranges correlates with protein, fat, carbohydrate, and water. This allows an accurate calculation of the calories of the analysis subject S by using the light having the wavelengths in the above ranges.

(4) The foodstuff analysis device 1 includes the wavelength limiter 24. This simplifies the structure of the foodstuff analysis device 1 compared to a structure in which the light receiver 22 spectrally measures light of unrestricted wavelengths.

(5) The calculation accuracy improves as the amount of light increases. However, the increased amount of light increasingly affects the analysis subject S. For example, the irradiation with light increases the temperature of the analysis subject S. Thus, the freshness of the analysis subject S may be reduced when the analysis subject S includes meat, fish, or the like. The property of the analysis subject S may be changed when the analysis subject S includes fat and oil, such as butter. Also, in general, temperature change may easily change the center of the absorption wavelength of water, which is mostly contained in a foodstuff or the like. This may lower the accuracy of calorie calculation.

The wavelength limiter 24 limits the wavelength of light before the light reaches the analysis subject S. Therefore, wavelengths that are not used for calculation of the absorbance do not reach the analysis subject S. This reduces the influence on the analysis subject S even when the analysis subject S is irradiated with the same amount of light.

(6) The foodstuff analysis device 1 includes the case 11, which shields the interior from light. This reduces the influence of near-infrared light from the exterior. Thus, decrease of the accuracy of calorie calculation may be limited.

Second Embodiment

A second embodiment of a foodstuff analysis device 1 differs from the first embodiment of the foodstuff analysis device 1 in the structure regarding the following aspects. The structure regarding the other aspects is the same. That is, the foodstuff analysis device 1 calculates the calories of the analysis subject S based on the weights of water and fat of the analysis subject S.

The wavelength limiter 24 includes the filter 25 corresponding to the first specified range and the filter 25 corresponding to the second specified range as the specified range. The absorbance in the first specified range clearly indicates water. The absorbance in the second specified range clearly indicates fat.

The controller 60 calculates the calories of the analysis subject S using the absorbance in the first specified range and the absorbance in the second specified range. The controller 60 stores, in advance, a relational equation of the absorbance in the first specified range and the weight of water based on chemical analyses performed on various types of foodstuffs. The controller 60 also stores, in advance, a relational equation of the absorbance in the second specified range and the weight of fat based on chemical analyses performed on various types of foodstuffs.

The process for calculating the calories of the analysis subject S will now be described.

The controller 60 calculates the weight of water in the analysis subject S (hereafter, "water amount W") based on the relational equation of the absorbance in the first specified range and the weight of water. The controller 60 also calculates the weight of water in the analysis subject S (hereafter, "fat weight F") based on the relational equation of the absorbance in the second specified range and the weight of fat.

The calorie coefficient of fat is 9. The calorie coefficient of protein is 4. The calorie coefficient of carbohydrate is 4. The calorie coefficient of fat is greater than those of protein and carbohydrate. Protein and carbohydrate have the same calorie coefficient. Thus, the calories derived from protein and the carbohydrate can be calculated without measuring each weight of protein and carbohydrate if the sum of the weights of protein and carbohydrate is estimated. The weight of a general foodstuff is mostly dominated by protein, carbohydrate, fat, and water. Therefore, the value obtained by subtracting the water amount W and the fat amount F from the total weight X of the analysis subject S substantially equals to the amount of protein and carbohydrate. The controller 60 calculates the calories C of the analysis subject S using equation (1) described below based on the water amount W and the fat amount F. The user inputs the total amount X using the operation unit 40.

$$C=(X-W-F)\times 4+F\times 9 \qquad (1)$$

The foodstuff analysis device 1 of the second embodiment has the following advantages in addition to advantages (1) to (6) of the first embodiment.

(7) The foodstuff analysis device 1 calculates calories using the absorbance of the specified wavelength in the first specified range and the absorbance of the specified wavelength in the second specified range.

The ratio of water in a general foodstuff is large. The calorie coefficient of fat is greater than those of protein and carbohydrate. Thus, the calories of the analysis subject S can be calculated using the absorbance of the specified wavelengths in the first specified range and the second specified range, which clearly indicates the weights of water and fat.

The foodstuff analysis device 1 calculates calories using only two specified ranges as the specified range. This simplifies an operational equation used to calculate calories compared to a structure that calculates calories using more than two specified ranges. Additionally, the accuracy of calorie calculation may be improved compared to a structure that calculates calories using only one specified range.

Third Embodiment

A third embodiment of a foodstuff analysis device 1 differs from the first embodiment of the foodstuff analysis device 1 in the structure regarding the following aspects. The structure regarding the other aspects is the same. That is, the foodstuff analysis device 1 calculates calories using transmitted light in addition to dispersed light.

Figure 7:
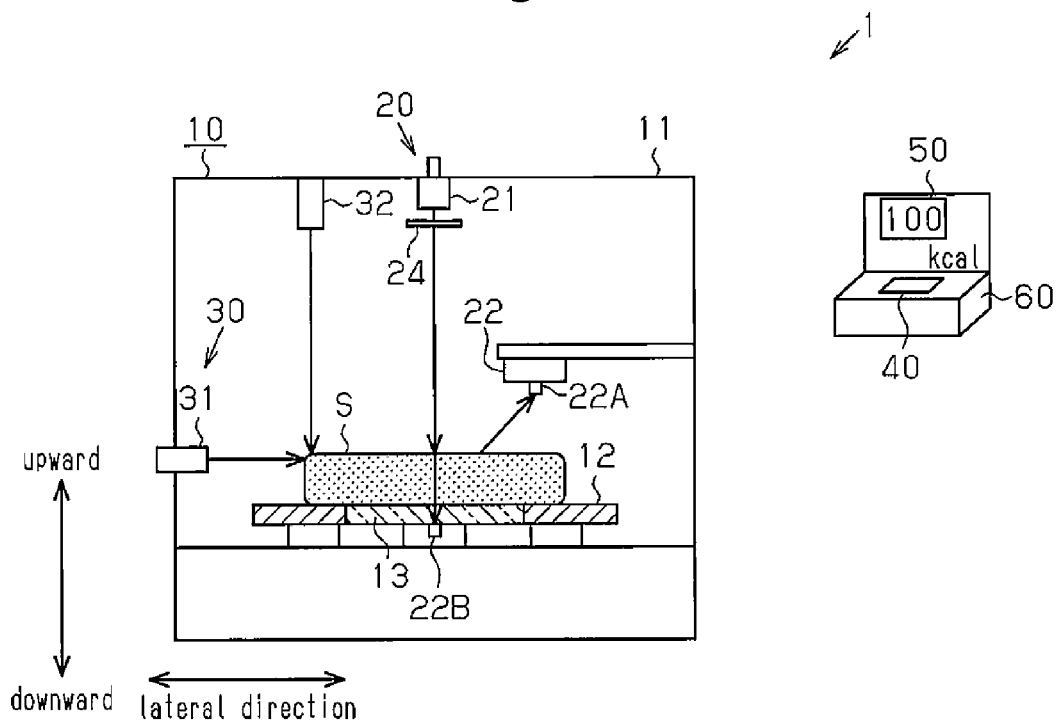
FIG. 7 is a schematic diagram of a third embodiment of a foodstuff analysis device according to the present invention showing the overall structure of the foodstuff analysis device.

As shown in FIG. 7, the light receiver 22 includes the light reception element 22A and a second light reception element 22B.

The second light reception element 22B is located below the sample plate 12. Some of the light emitted from the light emitter 21 toward the analysis subject S passes through the analysis subject S and is received by the second light reception element 22B. The second light reception element 22B transmits a signal that corresponds to the received light to the controller 60.

Figure 8:
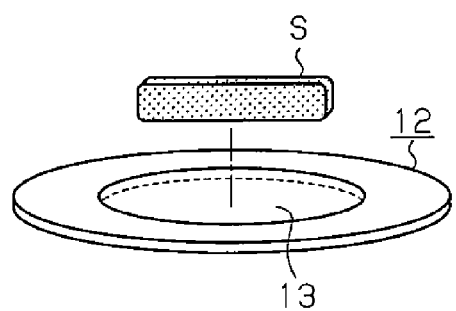
FIG. 8 is a perspective view of a sample plate of the third embodiment according to the present invention showing the overall structure of the sample plate.

As shown in FIG. 8, the sample plate 12 includes a transmission portion 13. The sample plate 12 is discoid. The transmission portion 13 is located in a central portion of the discoid shape of the sample plate 12. The transmission portion 13 is formed from a material that transmits near-infrared light. For example, quartz glass, which only slightly absorbs the light in the infrared range, may be used as the material of the transmission portion 13.

The controller 60 (refer to FIG. 1) calculates the calories of the analysis subject S based on an output signal from the light reception element 22A and an output signal from the second light reception element 22B. The calories are calculated using a relational equation and the amount of received light, which is obtained from the output signals from the light reception elements 22A and the second light reception element 22B.

The foodstuff analysis device 1 of the third embodiment has the following advantage in addition to advantages (1) to (6) of the first embodiment.

(8) The light receiver 22 includes the second light reception element 22B in addition to the light reception element 22A. This improves the accuracy of calorie calculation compared to a structure that calculates calories only using the light reception element 22A.

Other Embodiments

The present foodstuff analysis device includes embodiments other than the first embodiment, the second embodiment, and the third embodiment. Modified examples of each embodiment will now be described as other embodiments of the present foodstuff analysis device. Modified examples may be combined.

The foodstuff analysis device 1 of the second embodiment calculates calories using the absorbance of the specified wavelength in the first specified range and the absorbance of the specified wavelength in the second specified range. However, the foodstuff analysis device 1 is not limited to such a structure. For example, a modified example of the foodstuff analysis device 1 calculates calories using one of the absorbance of the specified wavelength in the first specified range and the absorbance of the specified wavelength in the second specified range. Instead of the absorbance of the specified wavelength in the first specified range and the absorbance of the specified wavelength in the second specified range, the calories may be calculated using the absorbance of the specified wavelength in at least one of the first to sixth specified ranges. The weight of carbohydrate may be calculated using the specified wavelengths that clearly indicate carbohydrate in the first to sixth specified ranges. Also, the weight of protein may be calculated using the specified wavelengths that clearly indicate protein in the first to sixth specified ranges.

The controller 60 of the second embodiment calculates calories using the water amount W and the fat amount F. However, the controller 60 is not limited to such a structure. For example, a modified example of the controller 60 calculates calories using food type information in addition to the water amount W and the fat amount F. For example, salad, rice, bread, and the name of a dish, such as hamburger steak, are set as the food type information.

The controller 60 stores a plurality of pieces of the food type information in advance. An operator operates the operation unit 40 to select a food type that corresponds to the type of the analysis subject S from the pieces of the food type information. The controller 60 calculates calories based on the selected food type information. For example, equation (2) described below is used as the equation for calculating calories. The foodstuff analysis device 1 of the modified example improves the accuracy of calorie calculation compared to a structure that calculates calories by measuring the components. Here, "T" denotes a correction value that is set for each food type. The present modified example is referred to as the modified example X.

$$C=(S-W-F-T)\times 4+F\times 9 \qquad (2)$$

The modified example X may be further modified as follows. A modified example of the foodstuff analysis device 1 includes a camera. The controller 60 processes an image of the camera to detect the food type information of the analysis subject S. For example, when green occupies a predetermined area of the image or more, the controller 60 selects salad from the pieces of the food type information stored in advance.

The foodstuff analysis device 1 of the second embodiment calculates calories using the value obtained by subtracting the water amount W and the fat amount F from the total weight X in equation (1) as the sum of the weights of protein and carbohydrate. However, the foodstuff analysis device 1 is not limited to such a structure. For example, a modified example of the foodstuff analysis device 1 obtains a value by subtracting a small value, such as salt, in addition to the water amount W and the fat amount F from the total weight X. The modified example uses the obtained value as the sum of the weights of protein and carbohydrate to calculate calories. The calorie coefficient of salt is zero. This improves the accuracy of calorie calculation by calculating calories using the value obtained by subtracting the amount of salt from the total weight X. The weight of salt may be calculated using the measurement unit 20. Alternatively, the weight of salt may be stored in advance in the controller 60 as the average amount of salt of a foodstuff.

The foodstuff analysis device 1 of the second embodiment displays calories. However, the foodstuff analysis device is not limited to such a structure. For example, a modified example of the foodstuff analysis device 1 displays the weights of water, fat, carbohydrate, and protein. In this case, the controller 60 need not calculate calories.

The foodstuff analysis device 1 of the first embodiment and the third embodiment calculates calories using the absorbance in the first specified range to the ninth specified range. However, the foodstuff analysis device 1 is not limited to such a structure. For example, a modified example of the foodstuff analysis device 1 calculates calories using the absorbance in at least one of the first specified range to the ninth specified range.

The foodstuff analysis device 1 of the first embodiment and the third embodiment calculates calories using the absorbance in the specified range. However, the foodstuff analysis device 1 is not limited to such a structure. For example, a modified example of the foodstuff analysis device 1 calculates calories using the absorbance of wavelengths at fixed intervals of 700 to 1100 nm.

Figure 9:
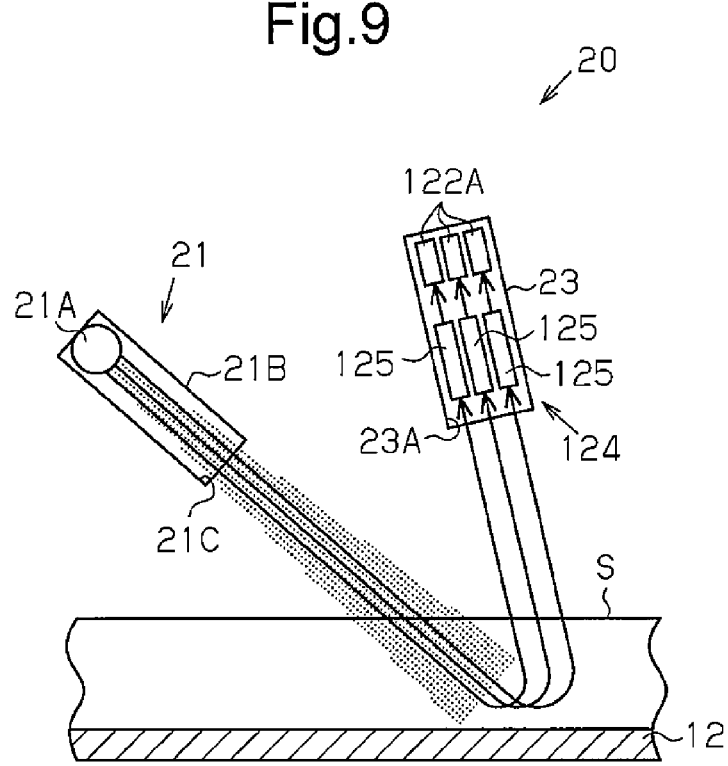
FIG. 9 is a schematic diagram of another embodiment of a measurement unit according to the present invention showing the overall structure of the measurement unit.

The wavelength limiter 24 of the first embodiment and the second embodiment limits the wavelength of light before the light reaches the analysis subject S. However, the wavelength limiter 24 is not limited to such a structure. For example, as shown in FIG. 9, a modified example of a wavelength limiter 124 limits the wavelength of light to the specified range after the light emitted from the light emitter 21 reaches the analysis subject S and before the light emitted from the light emitter 21 is received by the light receiver 22. More specifically, the wavelength limiter 124 includes a plurality of filters 125 that correspond to specified ranges differing from one another in the cylinder portion 23. A light reception element 122A receives the light having a wavelength restricted by each filter 125. In this case, the light reception element 122A may be arranged for each filter 125. Alternatively, one light reception element 122A may be arranged and sequentially switch the filters 125. In the present modified example, ambient light, such as the sun light, only slightly affects the light reception element 122A. Thus, the foodstuff analysis device 1 of the present modified example may be used outside. The foodstuff analysis device 1 of the present modified example, which is only slightly affected by the ambient light, can accurately calculate calories even when the case 11 is omitted. The present modified example is referred to as the modified example Y.

The wavelength limiter 124 of the modified example Y includes the filters 125 that transmit the wavelengths in the specified ranges. However, the wavelength limiter 124 is not limited to such a structure. For example, a further modified example of the wavelength limiter 124 includes a prism instead of the filter 125. The wavelength limiter 124 changes the wavelength of light that reaches the light reception element 122A by adjusting the position of the prism and the position of the light reception element 122A.

Figure 10:
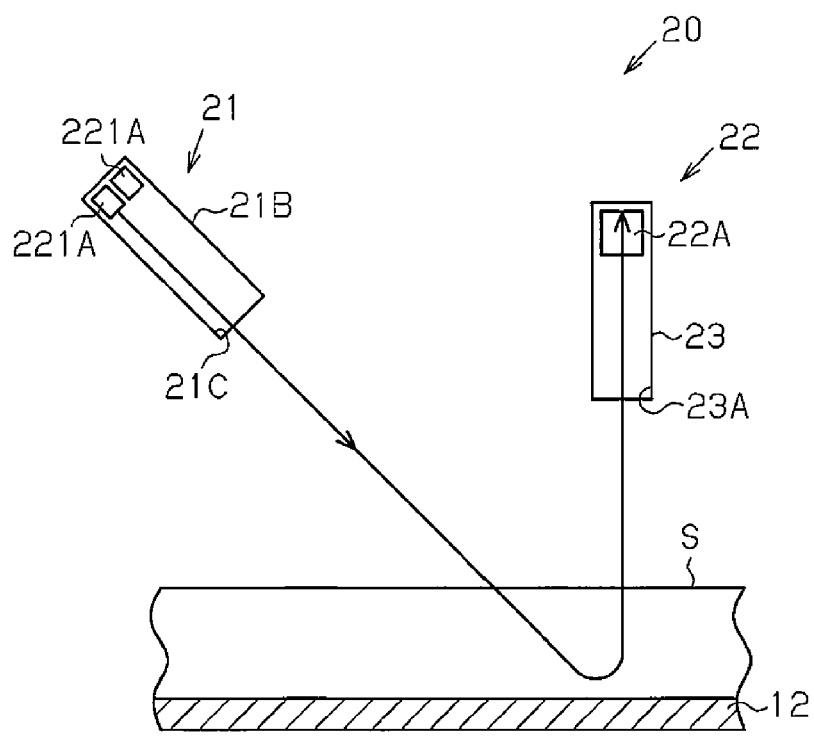
FIG. 10 is a schematic diagram of another embodiment of a measurement unit according to the present invention showing the overall structure of the measurement unit.

The foodstuff analysis device 1 of each embodiment includes the wavelength limiter 24. However, the foodstuff analysis device 1 is not limited to such a structure. For example, as shown in FIG. 10, a modified example of the foodstuff analysis device 1 emits the light only in the specified range in which the specified wavelength is the main component. More specifically, the foodstuff analysis device 1 includes a plurality of LEDs as light sources 221A. The LED emits the light having the wavelength in the specified range. The controller 60 sequentially switches the LEDs to emit light. In this case, instead of the LED, a laser beam may be used as the light source 221A. In the present modified example, other wavelengths only slightly affect the light reception element 22A. Thus, the absorbance may be accurately calculated.

The following structure may be added to the foodstuff analysis device 1 of each embodiment. That is, the foodstuff analysis device 1 includes a weight detector. The weight detector includes a piezoelectric element. The weight detector is located below the sample plate 12. An upper surface of the weight detector receives the sample plate 12. The pressure corresponding to the weights of the sample plate 12 and the analysis subject S placed on the sample plate 12 is applied to the weight detector. The piezoelectric element provides the controller 60 with a signal that corresponds to the pressure resulting from the weights of the sample plate 12 and the analysis subject S placed on the sample plate 12. The controller 60 calculates the weight of the analysis subject S based on the signal from the piezoelectric element of the weight detector. The controller 60 calculates calories using the weight of the analysis subject S. More specifically, the calories calculated using the absorbance is corrected based on the weight. This further improves the accuracy of calorie calculation. The present modified example is referred to as the modified example Z.

The modified example Z may replace the weight detector with a volume detector that measures the volume of the analysis subject. In this case, the controller 60 calculates calories using the volume of the analysis subject S.

The foodstuff analysis device 1 of each embodiment adjusts the position and the irradiation angle of the light emitter 21 based on the position of the analysis subject S measured by the position sensors 31 and 32. However, the foodstuff analysis device 1 is not limited to such a structure. For example, a modified example of the foodstuff analysis device 1 includes a motion mechanism that moves the sample plate 12 upward, downward, rightward, and leftward. The controller 60 changes the position of the sample plate 12 using the motion mechanism. The controller 60 changes the position of the analysis subject S based on a value detected by the position sensor 30. The motion mechanism may have a manually driven structure.

In the foodstuff analysis device 1 of each embodiment, the position sensor 30 is coupled to the interior of the case 11. However, the foodstuff analysis device 1 is not limited to such a structure. For example, in a modified example of the foodstuff analysis device 1, the position sensor 30 is coupled to at least one of the light emitter 21 and the light receiver 22.

The foodstuff analysis device 1 of each embodiment includes the position sensors 31 and 32. However, the foodstuff analysis device 1 is not limited to such a structure. For example, at least one of the position sensors 31 and 32 is omitted from a modified example of the foodstuff analysis device 1. When both of the position sensors 31 and 32 are omitted, the position and the angle of the light emitter 21 may be set to constantly irradiate the entire sample plate 12. In this case, the foodstuff analysis device 1 need not adjust the position and the angle of the light emitter 21.

The foodstuff analysis device 1 of each embodiment may include a modified example to which the following structure is added. That is, the modified example of the foodstuff analysis device 1 calculates calories using a reference sample. More specifically, a user prepares a reference sample the spectrum data of which changes in the same manner as the analysis subject S corresponding to the environment, such as temperature and humidity. The user measures the calories of the reference sample before measuring the analysis subject S. For example, when the analysis subject S is liquid, water is used as the reference sample. The controller 60 compares the calculated calories of the reference sample with the standard calories of the reference sample stored in advance and determines a correction coefficient. The controller 60 corrects the calculated calories using the correction coefficient determined by the reference sample when calculating the calories of the analysis subject S. This limits reduction of the accuracy of calorie calculation caused by the environment, such as temperature and humidity. The present modified example is referred to as the modified example V.

The foodstuff analysis device 1 of the modified example V determines the correction coefficient using the calories of the reference sample. However, the foodstuff analysis device 1 is not limited to such a structure. For example, a further modified example of the foodstuff analysis device 1 changes the position and light intensity of the light emitter using the calories of the reference sample. More specifically, the position and the light intensity of the light emitter are changed so that the calories of the reference sample conform to the calories of the reference sample stored in advance. This limits reduction of the accuracy of calorie measurement caused by the environment, such as temperature and humidity.

The foodstuff analysis device 1 of each embodiment includes one light emitter 21. However, the foodstuff analysis device 1 is not limited to such a structure. For example, a modified example of the foodstuff analysis device 1 includes a plurality of the light emitter 21.

The measurement unit 20 of each embodiment includes one light reception element 22A, which receives diffused and reflected light. However, the measurement unit 20 is not limited to such a structure. For example, a modified example of the measurement unit 20 includes more than one light reception element 22A.

The measurement unit 20 of each embodiment includes one cylinder portion 23. However, the measurement unit 20 is not limited to such a structure. For example, a modified example of the measurement unit 20 includes a plurality of cylinder portions 23 and an optical fiber. The optical fiber branches at one end. Each of the cylinder portions 23 is connected to one of the branched ends of the optical fiber. The other end of the optical fiber is connected to the light reception element 22A. The light reception element 22A collects the diffused and reflected light via each cylinder portions 23 and the optical fiber. The measurement unit 20 collects the diffused and reflected light that arrives at a plurality of portions. This increases the intensity of light that reaches the light reception element 22A.

The controller 60 of each embodiment calculates calories using the absorbance. However, the controller 60 is not limited to such a structure. For example, a modified example of the controller 60 calculates calories using the absorption amount of light instead of the absorbance.

The wavelength limiter 24 of each embodiment includes the filters 25 that transmit light of the wavelength in the specified range. However, the wavelength limiter 24 is not limited to such a structure. For example, a modified example of the wavelength limiter 24 includes one filter that includes a piezoelectric element. The application of electric stimulation to the piezoelectric element changes the wavelength of light that are allowed to pass through the filter 25.

The foodstuff analysis device 1 of each embodiment includes the display 50 having a liquid crystal window. The foodstuff analysis device 1 is not limited to such a structure. For example, a modified example of the foodstuff analysis device 1 includes a display 50 that has an LED. The display 50 may have any structure as long as the display 50 can show calculated calories.

The foodstuff analysis device 1 of each embodiment shows the calories of the analysis subject S on the display 50. However, the foodstuff analysis device 1 is not limited to such a structure. For example, a modified example of the foodstuff analysis device 1 includes a port that outputs a calculation result of calories to an external medium. For example, the port includes a USB port and a port for wireless communication.

The foodstuff analysis device 1 of each embodiment includes the sample plate 12. However, the foodstuff analysis device 1 is not limited to such a structure. For example, the sample plate 12 is omitted from a modified example of the foodstuff analysis device 1. In this case, the analysis subject S may be placed in a quartz glass container when the measurement is performed. Also, a holder that holds the analysis subject S may be fastened to the case 11.

The case 11 of each embodiment includes the door. However, the case 11 is not limited to such a structure. For example, the door is omitted from a modified example of the case 11. In this case, the foodstuff analysis device 1 may measure the absorbance when the analysis subject S is not located in the case 11. Such absorbance may be used as a value used to compare to the absorbance when the analysis subject S is measured. More specifically, the foodstuff analysis device 1 calculates the absorbance based on a value obtained by subtracting a value measured when the analysis subject S is not located in the case 11 from a value obtained when the analysis subject S is measured.

The foodstuff analysis device 1 of each embodiment includes the case 11. However, the foodstuff analysis device 1 is not limited to such a structure. For example, the case 11 is omitted from a modified example of the foodstuff analysis device 1.

The invention claimed is:

1. A foodstuff analysis device comprising:
    a light emitter that irradiates an analysis subject with light having a wavelength included in a range from 700 nm to 1100 nm;
    a light receiver that receives at least one of light reflected from the analysis subject and light passing through the analysis subject;
    a calculator that calculates an absorption amount of light received by the light receiver; and
    an analyzer that calculates calories of the analysis subject based on a correlation of the absorption amount of light and calorie and the absorption amount of light calculated by the calculator,
    wherein the calculator calculates the absorption amount of light having a specified wavelength in the light received by the light receiver,
    the foodstuff analysis device further comprises a wavelength limiter that limits a wavelength range of the light emitted from the light emitter to a specified range in which the specified wavelength is the main component, and
    the specified wavelength includes:
        a wavelength range from 940 to 1020 nm that indicates water of the analysis subject; and
        at least one of wavelength ranges from 910 to 940 nm, 890 to 930 nm, 970 to 1000 nm, 1000 to 1030 nm, 1030 to 1060 nm, 740 to 770 nm, 1010 to 1060 nm, and 890 to 950 nm,
    wherein the analyzer is configured to calculate calories of the analysis subject based on the absorption amount of light having the wavelength range from 940 to 1020 nm, and the absorption amount of light having at least one of the wavelength ranges from 910 to 940 nm, 890 to 930 nm, 970 to 1000 nm, 1000 to 1030 nm, 1030 to 1060 nm, 740 to 770 nm, 1010 to 1060 nm, and 890 to 950 nm.

2. The foodstuff analysis device according to claim 1, wherein the wavelength limiter limits the wavelength range of the light to the specified range before the light emitted from the light emitter reaches the analysis subject.

3. The foodstuff analysis device according to claim 1, wherein the wavelength limiter limits the wavelength range of the light to the specified range after the light emitted from the light emitter reaches the analysis subject and before the light emitted from the light emitter is received by the light receiver.

4. The foodstuff analysis device according to claim 1, wherein the light emitter irradiates the analysis subject only with light in the specified range in which the specified wavelength is the main component.

5. The foodstuff analysis device according to claim 1, further comprising a detector that performs at least one of a measurement of weight of the analysis subject and a measurement of volume of the analysis subject,
    wherein the analyzer calculates calories of the analysis subject or a component amount of the analysis subject using a measurement result of the detector.

6. The foodstuff analysis device according to claim 1, wherein the analyzer further calculates a component amount of the analysis subject based on a correlation of the absorption amount of light and the component amount of a foodstuff and the absorption amount of light calculated by the calculator.

* * * * *